United States Patent
Bankers et al.

(10) Patent No.: US 7,440,683 B2
(45) Date of Patent: Oct. 21, 2008

(54) VAPOR-EMITTING DEVICE WITH AN ACTIVE END OF USE INDICATOR

(75) Inventors: Jeffrey Bankers, Scottsdale, AZ (US);
Perry Kaiser, Scottsdale, AZ (US);
Kevin Hafer, Phoenix, AZ (US); Carl Triplett, Scottsdale, AZ (US)

(73) Assignee: The Dial Corporation, Scottsdale, AZ (US)

( * ) Notice: Subject to any disclaimer, the term of this patent is extended or adjusted under 35 U.S.C. 154(b) by 99 days.

(21) Appl. No.: 11/421,982

(22) Filed: Jun. 2, 2006

(65) Prior Publication Data
US 2007/0058956 A1    Mar. 15, 2007

Related U.S. Application Data

(63) Continuation of application No. 11/162,522, filed on Sep. 13, 2005, and a continuation of application No. 11/162,519, filed on Sep. 13, 2005, now Pat. No. 7,164,849.

(51) Int. Cl.
*F22B 1/20* (2006.01)
*A01G 13/06* (2006.01)

(52) U.S. Cl. .................... 392/386; 392/390; 392/392
(58) Field of Classification Search .................. None
See application file for complete search history.

(56) References Cited

U.S. PATENT DOCUMENTS

| 3,780,260 | A | 12/1973 | Elsner |
| 5,546,926 | A | 8/1996 | Lake |
| 5,647,052 | A | 7/1997 | Patel et al. |
| 6,368,564 | B1 | 4/2002 | Smith |
| 2004/0005146 | A1 | 1/2004 | Wefler |

*Primary Examiner*—Thor S Campbell
(74) *Attorney, Agent, or Firm*—Snell & Wilmer L.L.P.

(57) ABSTRACT

Vapor-emitting devices according to various embodiments of the invention include active end of use indicators to warn users that it is nearing the time and/or time to replace the vapor-emitting device or a refill for the device. Some embodiments of the vapor-emitting devices include intrusive actuation of the end of use indicator, while other embodiments include non-intrusive actuation of the end of use indicator. The indicators may be visual and/or auditory cues for notifying users it is nearing the time and/or time to replace the vapor-emitting device or a refill for the device.

16 Claims, 9 Drawing Sheets

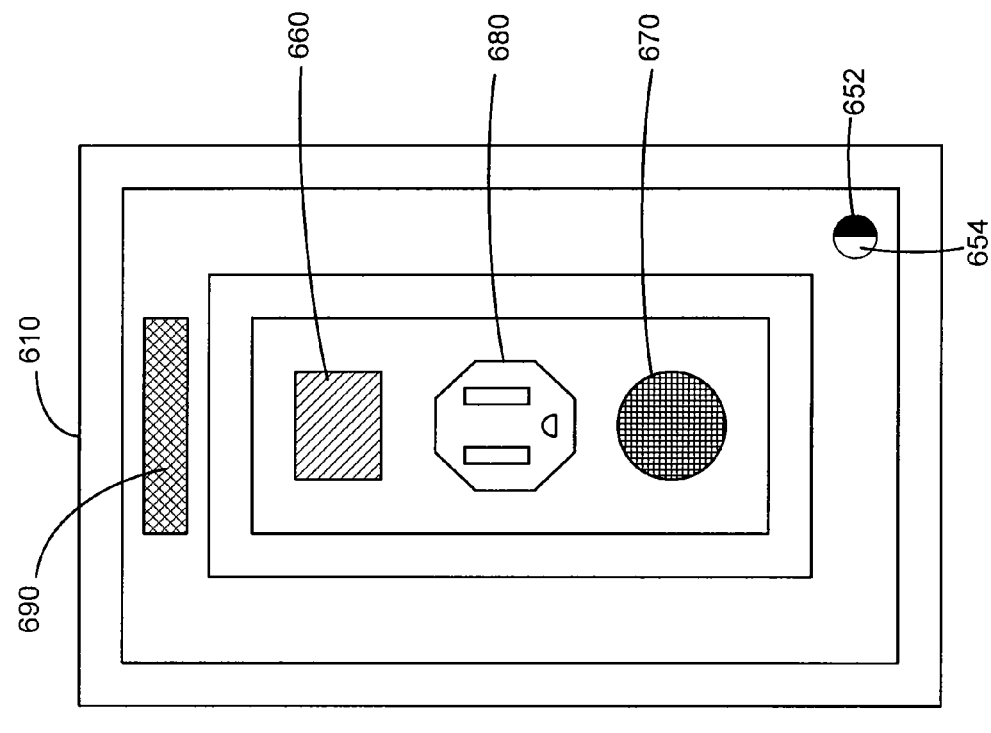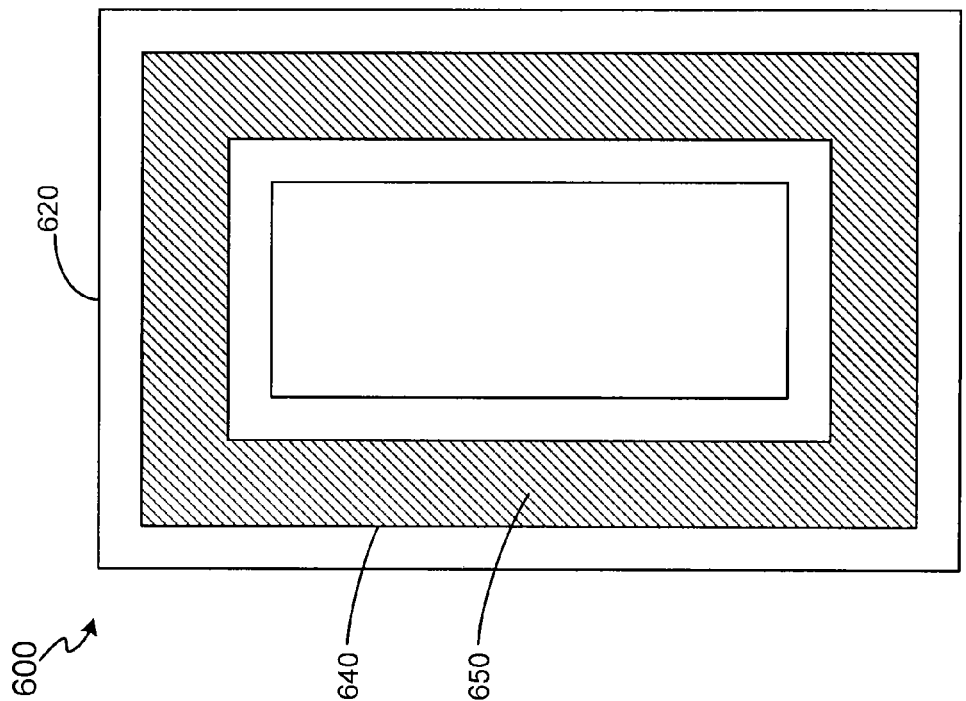
FIG. 6

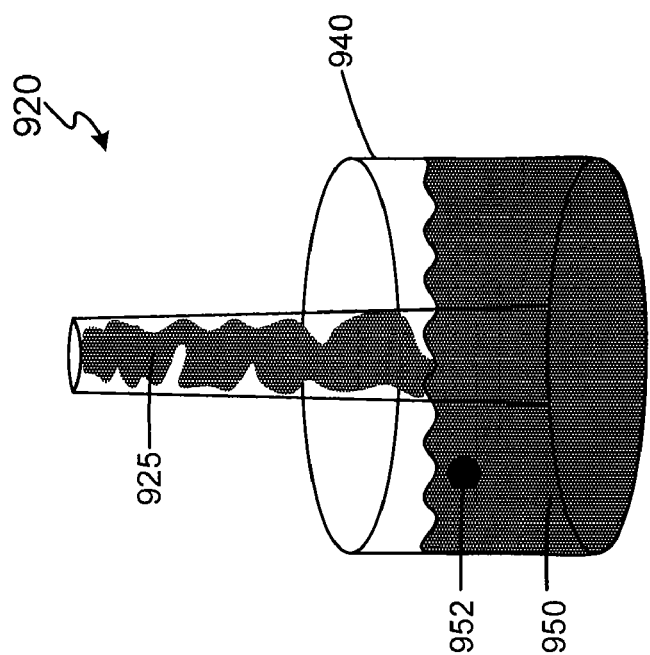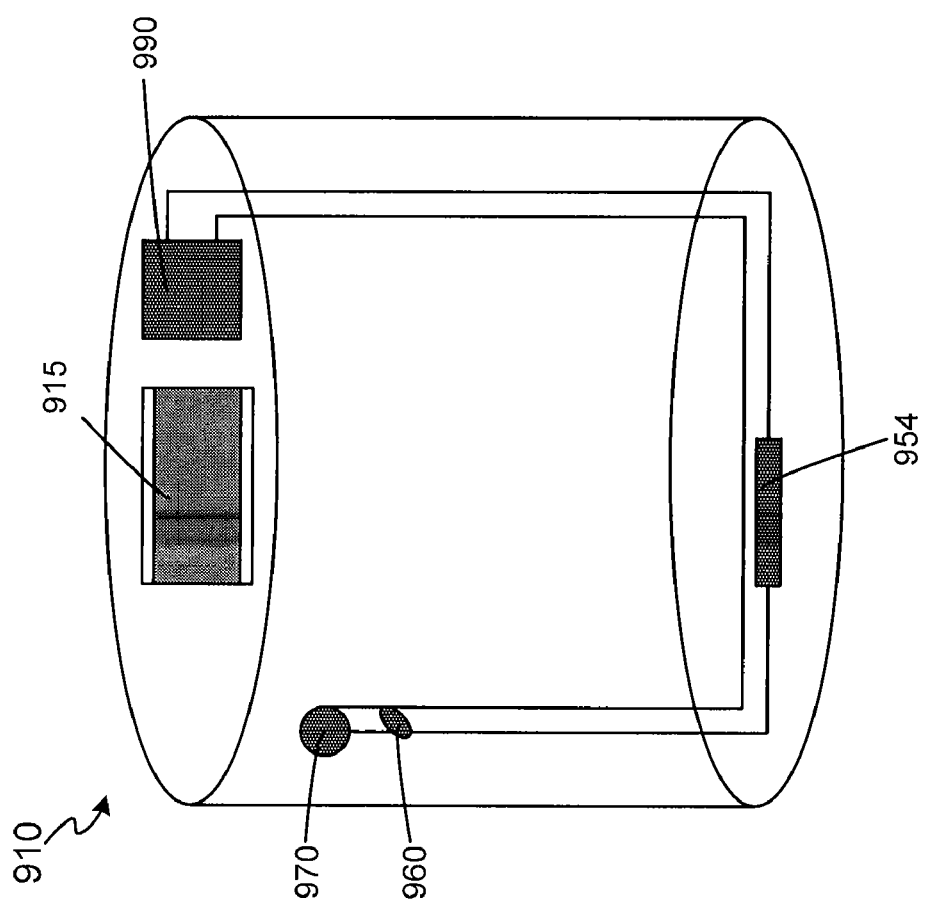
FIG. 9

VAPOR-EMITTING DEVICE WITH AN ACTIVE END OF USE INDICATOR

CROSS REFERENCE TO RELATED APPLICATIONS

This application is a continuation of U.S. Utility patent application Ser. No. 11/162,522 entitled, "VAPOR-EMITTING DEVICE WITH A SOLAR-POWERED, ACTIVE END OF USE INDICATOR," filed Sep. 13, 2005 and U.S. patent application Ser. No. 11/162,519, now U.S. Pat. No. 7,164,849 entitled "VAPOR-EMITTING DEVICE WITH AN ACTIVE END OF USE INDICATOR," filed Sep. 13, 2005 all of which are incorporated herein by reference.

FIELD OF THE INVENTION

The invention generally relates to vapor-emitting devices, and particularly to, vapor-emitting devices including an active end of use indicator.

BACKGROUND OF THE INVENTION

Vapor-emitting devices are generally used to emit an environment-altering fragrance, an insect repellant, and/or the like. Typically, to know when it is time to replace the vapor-emitting device or a refill for the vapor-emitting device, users are required to take the initiative to visually inspect the contents and/or refill of the vapor-emitting device. There are, however, at least a few problems associated with such a requirement, 1) users must remember that it is nearing the time and/or time to replace/refill the vapor-emitting device; 2) users must personally inspect the vapor-emitting device and/or refill to determine if it is nearing the time and/or time to replace/refill the vapor-emitting device; and 3) upon inspection, users must have the capability of determining that indeed the vapor-emitting device contains a low amount of volatizable material and/or is no longer emitting vapor, which may be difficult if the volatizable material is not readily visible and/or leaves a residue making it difficult to determine how much, if any, volatizable material remains.

As discussed above, current devices neither actively warn users that the vapor-emitting device is low on volatizable material or is no longer producing vapor and/or actively remind users that it is time to replace the vapor-emitting device or a refill for the device. Therefore, there is a need for a vapor-emitting device that actively warns users that the device is low on volatizable material and/or no longer producing vapor such that users will be put on notice that it is nearing the time or time to replace the vapor-emitting device or a refill for the device.

SUMMARY OF THE INVENTION

A vapor-emitting device according to various exemplary embodiments of the present invention includes a reservoir housing a volatizable material and an active end of use indicator in communication with the reservoir, wherein the active end of use indicator is configured to alert a user that the reservoir includes a low level of volatizable material and/or the reservoir is empty. In various exemplary embodiments, the active end of use indicator is connected to a power source. In accordance with an aspect of one exemplary embodiment of the invention, the power source may be a solar cell. In accordance with other aspects of the invention, the power source may be a battery, an electrical outlet, or any other device capable of supplying power to the active end of use indicator.

BRIEF DESCRIPTION OF THE DRAWINGS

Additional embodiments of the invention will become evident upon reviewing the non-limiting embodiments described in the specification in conjunction with the accompanying figures, wherein:

FIG. 6 is a diagram of another exemplary embodiment of a vapor-emitting device including a non-intrusive end of use indicator;

FIG. 9 is a diagram of one exemplary embodiment of a vapor-emitting device 900 including a solar-powered, active end of use indicator.

DETAILED DESCRIPTION OF THE INVENTION

The detailed description of exemplary embodiments of the invention herein makes reference to the accompanying figures, which show the exemplary embodiment by way of illustration and its best mode. While these exemplary embodiments are described in sufficient detail to enable one skilled in the art to practice the invention, it should be understood that other embodiments may be realized, and that logical and/or mechanical changes may be made without departing from the spirit and scope of the invention. Thus, the detailed description herein is presented for purposes of illustration only and not by way of limitation.

For the sake of brevity, functional embodiments of the apparatus and systems (and components of the individual operating components of the systems) may not be described in detail herein. Furthermore, the connecting lines shown in the various figures contained herein are intended to represent exemplary functional relationships and/or physical connections between the various elements. It should be noted that many alternative or additional functional relationships or physical connections may be present in a practical system.

Various embodiments of the invention include vapor-emitting devices (e.g., air fresheners, emanators, evaporators, foggers, and the like). In exemplary embodiments, these vapor-emitting devices are configured to alert a user that it is time and/or nearing the time to replace a refill for the device, or replace the device itself in non-refillable embodiments. To alert the user, these vapor-emitting devices include an end of use indicator that is actuated when the device includes a pre-determined level of voltatizable material and/or when the device is empty.

Figure 1:
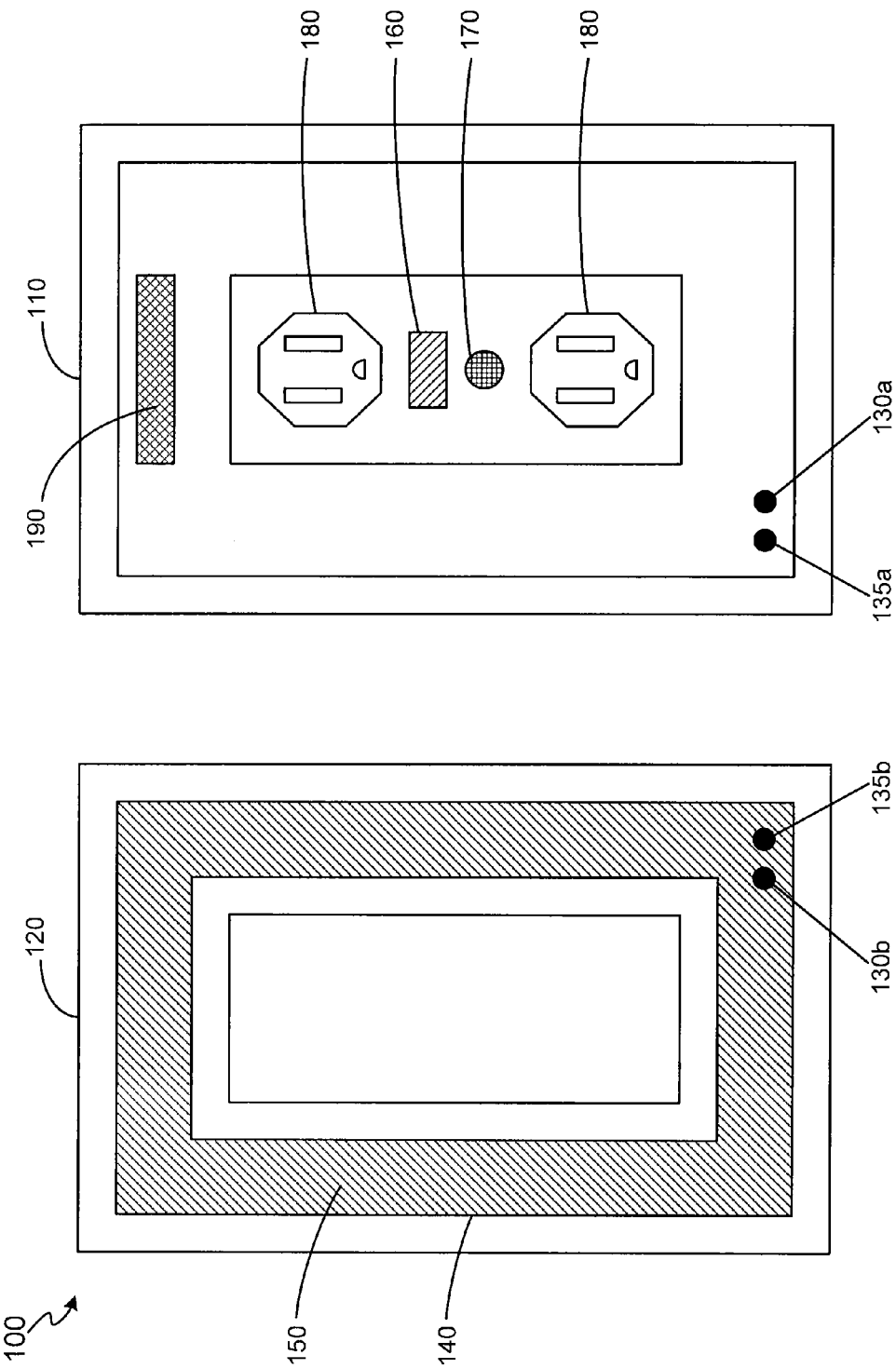
FIG. 1 is a diagram of an exemplary embodiment of a vapor-emitting device including an intrusive end of use indicator.

Turning now to the figures, FIG. 1 is a diagram of an exemplary embodiment of a vapor-emitting device 100 including an intrusive end of use indicator. Vapor-emitting device 100 may be any device and/or components known in the art capable of evaporating a volatizable material (e.g., a fragrance, insecticide, insect repellant, and the like). In various exemplary embodiments, vapor emitting device 100 includes a wick (not shown) in communication with an evaporating element (not shown) such that the wick provides a volatizable material (e.g., volatizable material 150, discussed below) to the evaporating element for vaporization. In other exemplary embodiments, vapor-emitting device 100 is a passive vapor-emitting device such that the volatizable material (e.g., volatizable material 150, discussed below) is caused to be evaporated.

In one exemplary embodiment, vapor-emitting device 100 includes non-refill portion 110 and a refill portion 120. Non-refill portion 110, in one exemplary embodiment, includes an electrode 130a and an electrode 135a, both of which may be any type of electrode known in the art capable of actuating a warning device. Furthermore, refill portion 120 includes an electrode 130b and an electrode 135b, both of which may be any type of electrode known in the art capable of actuating a warning device, and complementary to electrodes 130a and 135a, respectively. In other words, when refill portion 120 is appropriately connected to non-refill portion 110, electrode 130a is connected to electrode 130b, and electrode 135a is connected to electrode 135b. Notably, FIG. 1 illustrates an anterior view of one embodiment of non-refill portion 110, and a posterior view of one embodiment of refill portion 120.

Electrodes 130b and 135b, in one exemplary embodiment, are oriented within a reservoir 140 of refill portion 120. In accordance with one exemplary embodiment, reservoir 140 stores a volatizable material 150 to be evaporated by or caused to be evaporated within vapor-emitting device 100. Volatizable material 150 may be any volatizable material known in the art capable of, for example, altering the scent in an environment (e.g., a fragrance) and/or discouraging insects and other creatures from being present in the environment (e.g., an insecticide, an insect repellant, and the like). In one exemplary embodiment, volatizable material 150 includes an electrolyte such that volatizable material 150 is capable of conducting electrons between electrodes 130b and 135b. In other words, when sufficient volatizable material 150 is present within reservoir 140 (i.e., when volatizable material 150 is in contact with both electrode 130b and electrode 135b), a complete electrical circuit (not shown in detail) is formed. Likewise, when volatizable material 150 is not in contact with both electrode 130b and 135b, the electrical circuit is disrupted. Examples of suitable electrolytes included within volatizable material 150 include, but are not limited to, quaternary amines (e.g., tetraethylammonium chloride), alkyl halides (e.g., sodium chloride), transition metal salts (e.g., ferric chloride), and the like.

Vapor-emitting device 100 includes an active end of use indicator to proactively alert a user that reservoir 140 includes a low level of volatizable material and/or reservoir 140 is empty, which may include any suitable end of use indicator and/or components known in the art. In one exemplary embodiment, the end of use indicator is a light 160. Light 160 may be any known light and/or device known in the art capable of being illuminated and/or visually alerting a user. In accordance with an aspect of one exemplary embodiment, light 160 may be a light emitting diode (LED). In other aspects of the invention, light 160 may be a liquid crystal display (LCD), an incandescent light, a halogen light, a fluorescent light, and the like. Furthermore, light 160 may be any size (i.e., dimensions) and power (i.e., wattage) suitable for alerting the user. Moreover, light 160 may be any color, although it is preferable that light 160 include a color that is different and distinct from the primary color of vapor-emitting device 100. For example, if vapor-emitting device 100 is white, light 160 may be red, green, blue, yellow, purple, pink, black, brown, or orange.

In another exemplary embodiment, the end of use indicator is an audible device 170, which may be any device and/or component capable of emitting sound. In accordance with an aspect of one exemplary embodiment, audible device 170 may be a speaker capable of emitting a continuous or intermittent sound/noise. In another aspect of the invention, audible device 170 may include a voice to alert the user. Notably, and as illustrated in FIG. 1, vapor-emitting 100 may include both light 160 and audible device 170 to alert the user that reservoir 140 includes a low level of volatizable material 150 and/or reservoir 140 is empty.

In addition, vapor-emitting device 100 may include one or more plug receptacles 180. Plug receptacles 180 may be any plug receptacle known in the art capable of having an electric plug inserted within it and providing electric current to the device connected to the plug. As such, plug receptacles 180, in one embodiment, are configured to function similar to standard plug receptacles found, for example, in a wall or on a power strip. Thus, plug receptacles 180 may also function to mimic a standard outlet such that vapor-emitting device 100 is less likely to be detected as a vapor-emitting device. In another embodiment, plug receptacles 180 are not functional, but are simply configured to mimic the standard outlet similar to the embodiment discussed above. Notably, vapor-emitting device 100 may include any shape and/or dimensions suitable for emitting environment-altering fragrances and/or insect repellant, insecticide, and/or the like. However, embodiments desiring that vapor-emitting device 100 mimic a standard duplex wall outlet, power strip, or quadplex should include dimensions (e.g., height, width, depth, and the like)/shapes (e.g., rectangular, square, and the like) similar to well-accepted dimensions/shapes for these outlets and/or dimensions/shapes less likely to be otherwise noticed.

In yet another exemplary embodiment, vapor-emitting device 100 includes a power source 190 connected to the active end of use indicator circuit (i.e., light 160 and/or audible device 170). Power source 190 may be any device known in the art capable of supplying power to the active end of use indicator. In accordance with an aspect of one exemplary embodiment, power source 190 is a solar cell suitably configured to supply power to the active end of use indicator. In another aspect of the invention, power source 190 may be a battery or an electrical outlet with which vapor-emitting device 100 is connected.

Various embodiments of vapor-emitting device 100 function such that when sufficient volatizable material 150 is present in reservoir 140, the electrolytes within volatizable material 150 are capable of completing the circuit comprised of electrodes 130a and 130b, electrodes 135a and 135b, and the end of use indicator (e.g., light 160, audible device 170, and/or the like), wherein the circuit is suitably configured not to actuate the end of use indicator when the circuit is complete. However, when sufficient volatizable material 150 is not present within reservoir 140 such that the circuit is disrupted, the circuit is configured to actuate the end of use indicator. For example, when volatizable material 150 is not contacting both electrode 130b and electrode 135b, the end of use indicator may illuminate (e.g., when the end of use indicator is light 160), and/or emit a continuous or intermittent sound (e.g., when the end of use indicator is audible device 170 (i.e., a speaker)) to alert the user that refill portion 120 or vapor-emitting device 100 needs to be replaced.

Notably, vapor-emitting device 100 has been described as including refill portion 120, however, vapor-emitting device 100 may not be refillable. As such, reservoir 140 would be included within non-refill portion 110, and vapor-emitting device 100 should be discarded when all or substantially all of volatizable material 150 is evaporated or caused to be evaporated. Moreover, the invention contemplates that light 160 may be illuminated while there is sufficient volatizable material 150 in reservoir 140 then become non-illuminated as a way of indicating end of use.

Figure 2:
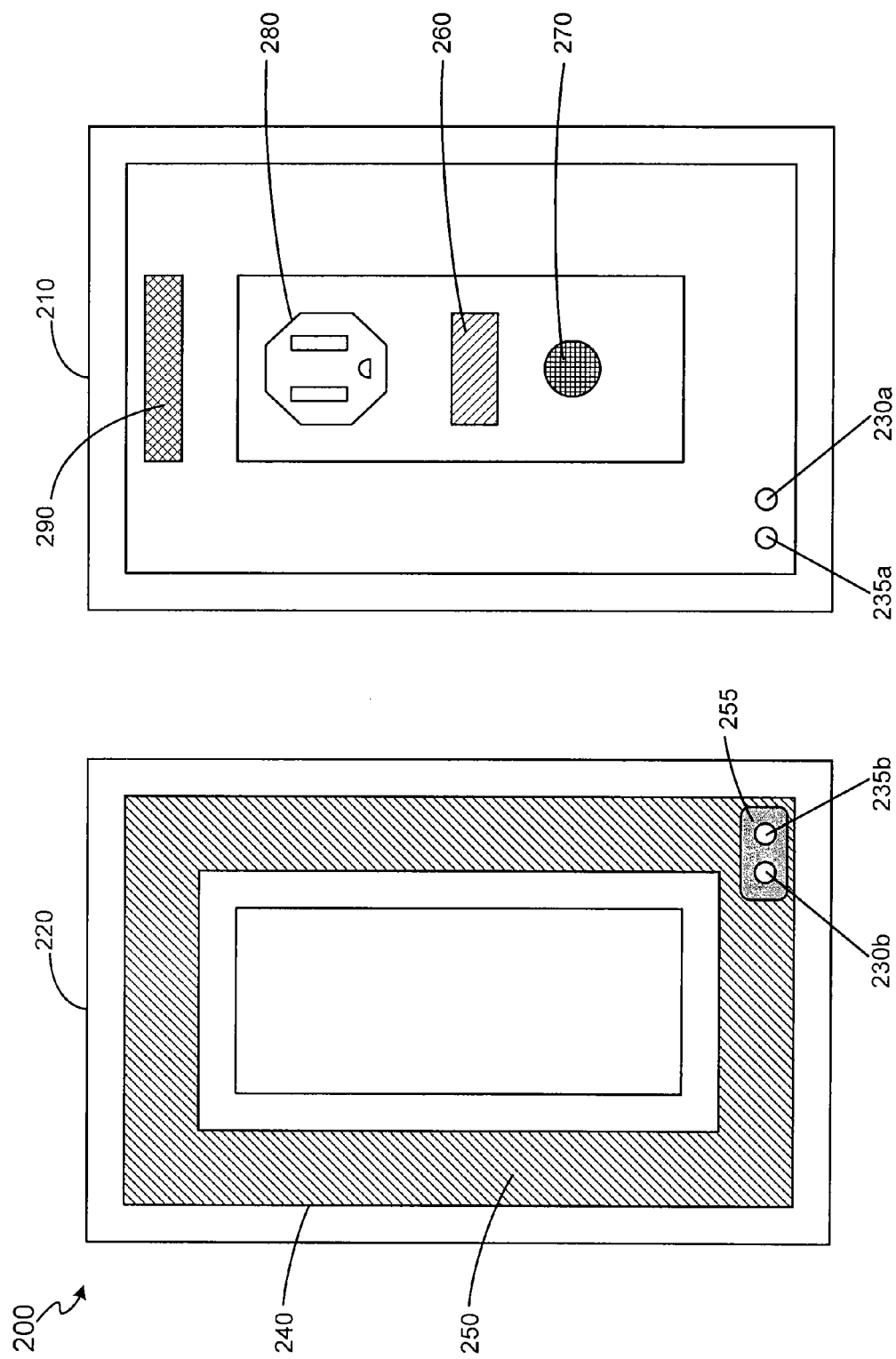
FIG. 2 is a diagram of another exemplary embodiment of a vapor-emitting device including an intrusive end of use indicator.

FIG. 2 is a diagram of another exemplary embodiment of a vapor-emitting device 200 including an intrusive end of use indicator. Vapor-emitting device 200 may be any device and/or components known in the art capable of evaporating a volatizable material or causing a volatizable material to be evaporated similar to vapor-emitting device 100 discussed above. Similar to FIG. 1, FIG. 2 illustrates an anterior view of one embodiment of a non-refill portion 210, and a posterior view of one embodiment of a refill portion 220.

Non-refill portion 210, in one exemplary embodiment, includes electrodes 230a and 235a similar to electrodes 130a and 135a discussed above, respectively. Furthermore, refill portion 220 includes electrodes 230b and 235b similar to electrodes 130b and 135b discussed above, respectively, proximate to one another and complementary to electrodes 230a and 235a. In one exemplary embodiment, when refill portion 220 is appropriately connected to non-refill portion 210, electrode 230a is connected to electrode 230b, and electrode 235a is connected to electrode 235b.

Electrodes 230b and 235b, in one exemplary embodiment, are oriented within a reservoir 240 of refill portion 220. In accordance with one exemplary embodiment, reservoir 240 stores a volatizable material 250 to be evaporated by or caused to be evaporated within vapor-emitting device 200. Volatizable material 250 may be any volatizable material known in the art capable of, for example, altering the scent in an environment (e.g., a fragrance) and/or discouraging insects and other creatures from being present in the environment (e.g., an insecticide, an insect repellant, and the like).

In another exemplary embodiment, reservoir 240 also includes an absorbent material 255 oriented in proximity to electrodes 230b and 235b. Absorbent material 255 may be any material capable of absorbing volatizable material 250 and expanding in size. Specifically, absorbent material 255 should be a material (e.g., a polymer) that, upon absorbing an amount of volatizable material 250, absorbent material 255 expands sufficient to disrupt the connection between electrode 230b and electrode 235b. In one exemplary embodiment, at least a portion of absorbent material 255 is carbon black. In accordance with an aspect of one exemplary embodiment of the invention, absorbent material 255 is a combination of carbon black and one or more suitable polymers.

Vapor-emitting device 200 includes an active end of use indicator to alert a user that reservoir 240 includes a low level of volatizable material 250 and/or reservoir 240 is empty, similar to embodiments of the active end of use indicator discussed above. In one exemplary embodiment, the end of use indicator is a light 260 similar to light 160 discussed above. In another exemplary embodiment, the end of use indicator is an audible device 270 similar to audible device 170 discussed above. Furthermore, vapor-emitting device 200 may include both light 260 and audible device 270 similar to embodiments of vapor-emitting device 100 discussed above. In addition, vapor-emitting device 200 may include one or more plug receptacles 280, and/or may be configured to mimic a standard outlet similar to plug receptacles 180 discussed above. Moreover, vapor-emitting device 200, in various embodiments, includes a power source 290 similar to power source 190 discussed above.

Various embodiments of vapor-emitting device 200 function such that when sufficient volatizable material 250 is present in reservoir 240, absorbent material 255 enlarges preventing electrode 230b from contacting electrode 235b, which effectively disrupts the end of use indicator circuit. When sufficient volatizable material 250 is not present within reservoir 240, absorbent material 255 contracts such that the end of use indicator circuit is completed (i.e., electrode 230b contacts electrode 235b), and the end of use indicator (e.g., light 260, audible device 270, and/or the like) is actuated. For example, when volatizable material 250 absorbed by absorbent material 255 is evaporated or caused to be evaporated, the connection between electrode 230b and electrode 235b is no longer disrupted and the end of use indicator may illuminate (e.g., when the end of use indicator is light 260) and/or emit a continuous or intermittent sound (e.g., when the end of use indicator is audible device 270 (i.e., a speaker)) to alert the user that refill portion 220 or vapor-emitting device 200 needs to be replaced.

Figure 3:
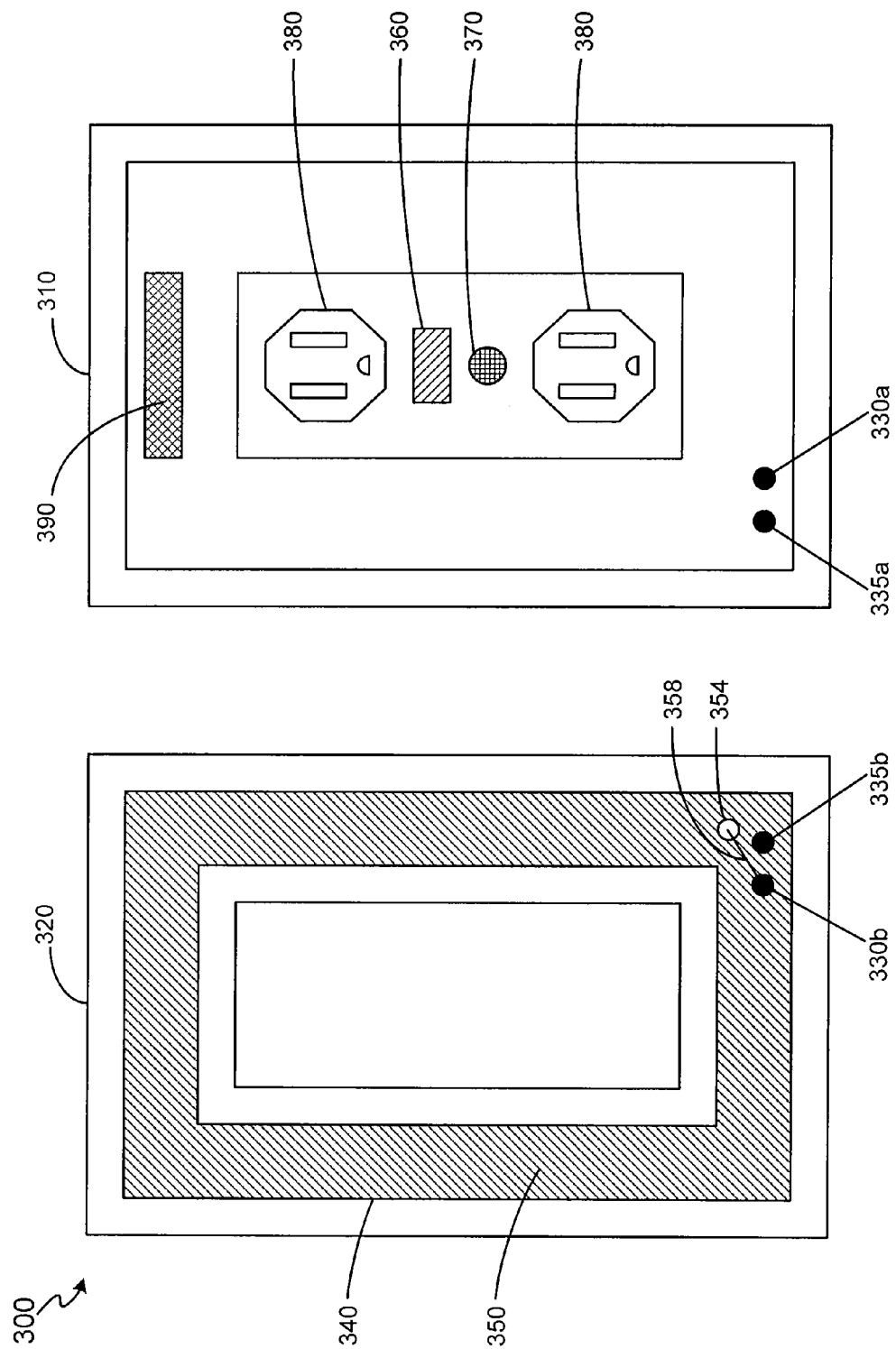
FIG. 3 is a diagram of yet another exemplary embodiment of a vapor-emitting device including an intrusive end of use indicator.

FIG. 3 is a diagram of yet another exemplary embodiment of a vapor-emitting device 300 including an intrusive end of use indicator. Vapor-emitting device 300 may be any device and/or components known in the art capable of evaporating a volatizable material or causing a volatizable material to be evaporated similar to vapor-emitting device 100 discussed above. Similar to FIG. 1, FIG. 3 illustrates an anterior view of one embodiment of a non-refill portion 310, and a posterior view of one embodiment of a refill portion 320.

Non-refill portion 310, in one exemplary embodiment, includes electrodes 330a and 335a similar to electrodes 130a and 135a discussed above. Furthermore, refill portion 320 includes electrodes 330b and 335b similar to electrodes 130b and 135b discussed above, respectively, proximate to one another and complementary to electrodes 330a and 335a. In one exemplary embodiment, when refill portion 320 is appropriately connected to non-refill portion 310, electrode 330a is connected to electrode 330b, and electrode 335a is connected to electrode 335b. Electrodes 330b and 335b, in one exemplary embodiment, are oriented within a reservoir 340 of refill portion 320.

In accordance with one exemplary embodiment, reservoir 340 stores a volatizable material 350 to be evaporated by or caused to be evaporated within vapor-emitting device 300. Volatizable material 350 may be any volatizable material known in the art capable of, for example, altering the scent in an environment (e.g., a fragrance) and/or discouraging insects and other creatures from being present in the environment (e.g., an insecticide, an insect repellant, and the like).

In another exemplary embodiment, reservoir 340 also includes a buoyant material 354 connected to electrode 330b via a conducting wire 358. Buoyant material 354 may be any hollow, solid, foamed and/or blown structure made of material(s) that when taken, in total, include a density lower than that of volatizable material 350. Furthermore, conducting wire 358 may be formed of any material known in the art capable of conducting electrical current. For example, conducting wire 358 may be formed of copper, aluminum, and the like.

Vapor-emitting device 300 includes an active end of use indicator to alert a user that reservoir 340 includes a low level of volatizable material 350 and/or reservoir 340 is empty, similar to embodiments of the end of use indicator discussed above. In one exemplary embodiment, the end of use indicator is a light 360 similar to light 160 discussed above. In another exemplary embodiment, the end of use indicator is an audible device 370 similar to audible device 170 discussed above. Furthermore, vapor-emitting 300 may include both light 360 and audible device 370 similar to embodiments of vapor-emitting device 100 discussed above. In addition, vapor-emitting device 300 may include one or more plug receptacles 380, and/or may be configured to mimic a standard outlet similar to plug receptacles 180 discussed above. Moreover, vapor-emitting device 300, in various embodiments, includes a power source 390 similar to power source 190 discussed above.

Various embodiments of vapor-emitting device 300 function such that as volatizable material 350 is evaporated, buoyant material 354 is caused to move towards electrode 335b. When volatizable material 350 is sufficiently evaporated (or caused to be evaporated), buoyant material 354 is caused to move such that conducting wire 358 contacts both electrode 330b and electrode 335b, thus completing the end of use indicator circuit. When the end of use indicator circuit is completed, the end of use indicator (e.g., light 360, audible device 370, and/or the like) is actuated (e.g., illuminated when the end of use indicator is light 360, and/or emits a continuous or intermittent sound when the end of use indicator is audible device 370 (i.e., a speaker)) to alert the user that refill portion 320 or vapor-emitting 300 needs to be replaced.

Figure 4:
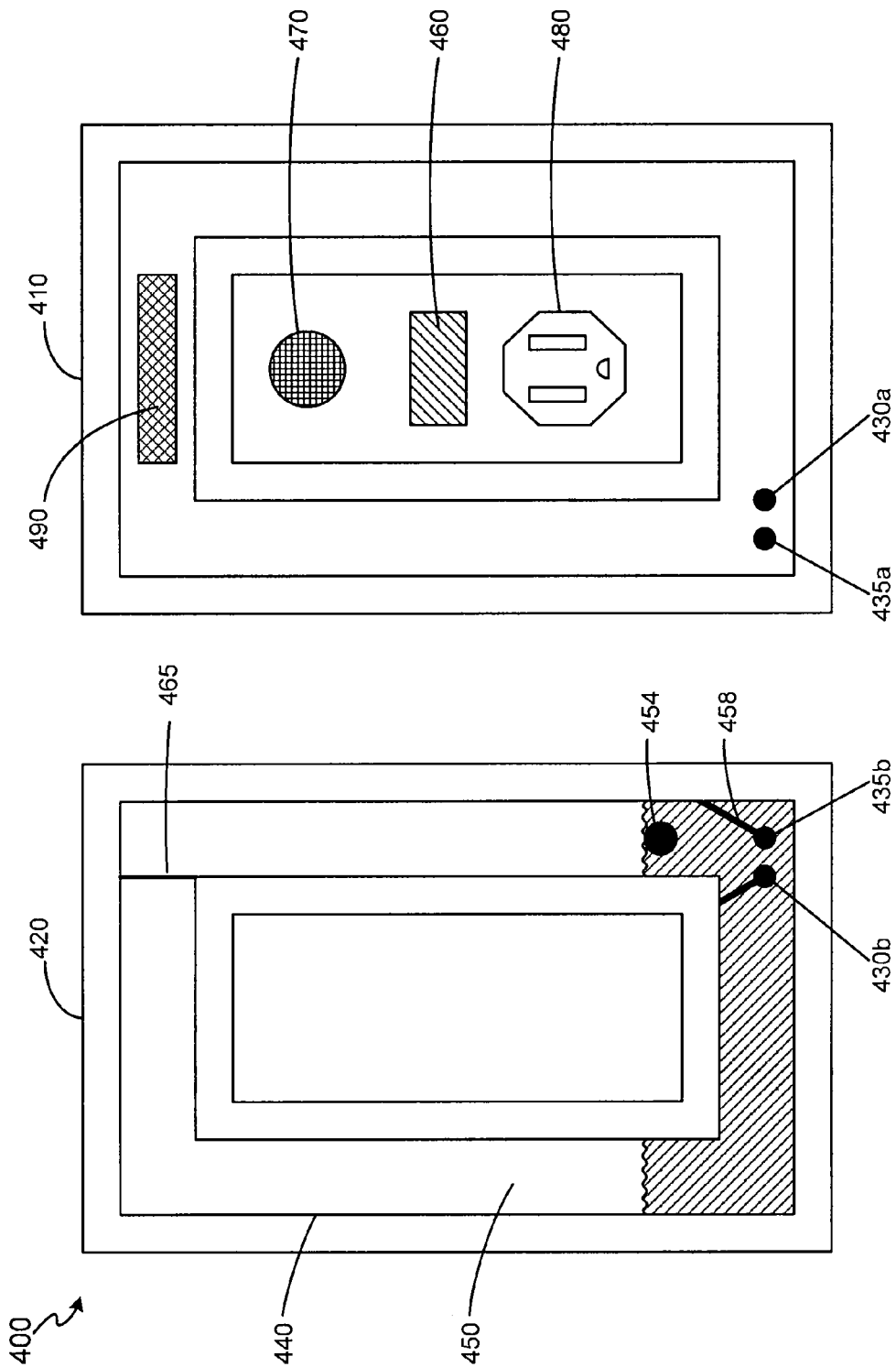
FIG. 4 is a diagram of still another exemplary embodiment of a vapor-emitting device including an intrusive end of use indicator.

FIG. 4 is a diagram of still another exemplary embodiment of a vapor-emitting device 400 including an intrusive end of use indicator. Vapor-emitting device 400 may be any device and/or components known in the art capable of evaporating a volatizable material or causing a volatizable material to be evaporated similar to vapor-emitting device 100 discussed above. Similar to FIG. 1, FIG. 4 illustrates an anterior view of one embodiment of a non-refill portion 410, and a posterior view of one embodiment of a refill portion 420.

Non-refill portion 410, in one exemplary embodiment, includes electrodes 430a and 435a similar to electrodes 130a and 135a discussed above. Furthermore, refill portion 420 includes electrodes 430b and 435b similar to electrodes 130b and 135b discussed above, respectively, oriented proximate to one another and complementary to electrodes 430a and 435a. In one exemplary embodiment, when refill portion 420 is appropriately connected to non-refill portion 410, electrode 430a contacts electrode 430b and electrode 435a contacts electrode 435b.

In accordance with one exemplary embodiment, reservoir 440 stores a volatizable material 450 to be evaporated by or caused to be evaporated within vapor-emitting device 400. Volatizable material 450 may be any volatizable material known in the art capable of, for example, altering the scent in an environment (e.g., a fragrance) and/or discouraging insects and other creatures from being present in the environment (e.g., an insecticide, an insect repellant, and the like).

In another exemplary embodiment, reservoir 440 also includes a buoyant conductive material 454. Buoyant conductive material 454 may be any hollow, solid, foamed and/or blown structure made of material(s) that is/are coated and/or blended with a conductive material such that that when taken, in total, the material includes a density lower than that of volatizable material 450. Examples of buoyant conductive material 454 include, but are not limited to, metals, carbon black, indium tin oxide, and the like.

Reservoir 440, in yet another exemplary embodiment, includes a funnel 458 configured to direct buoyant conductive material 454 towards electrodes 430b and 435b as volatizable material 450 is evaporated or caused to be evaporated. Notably, electrodes 430b and/or 435b are oriented such that they are spaced apart less than the diameter of buoyant conductive material 454 so that when buoyant conductive material 454 is directed by funnel 458 towards electrodes 430b and 435b, buoyant conductive material 454 will eventually contact both electrodes 430b and 435b.

In another embodiment, reservoir 440 includes a barrier 465 to prevent buoyant conductive material 454 from entering areas of reservoir 440 that will not direct buoyant conductive material 454 towards funnel 458. In various exemplary embodiments, funnel 458 and/or barrier 465 include pours/apertures (not shown) such that volatizable material 450 may flow through funnel 458 and/or barrier 465. As such, these pours/apertures should be large enough to allow volatizable material 450 to flow through, but small enough to prevent buoyant conductive material 454 from entering and/or becoming trapped with the pours/apertures.

Vapor-emitting device 400 also includes an active end of use indicator to alert a user that reservoir 440 includes a low level of volatizable material 450 and/or reservoir 440 is empty similar to embodiments of the end of use indicator discussed above. In one exemplary embodiment, the end of use indicator is a light 460 similar to light 160 discussed above. In another exemplary embodiment, the end of use indicator is an audible device 470 similar to audible device 170 discussed above. Furthermore, vapor-emitting 400 may include both light 460 and audible device 470 similar to embodiments of vapor-emitting device 100 discussed above. In addition, vapor-emitting device 400 may include one or more plug receptacles 480, and/or may be configured to mimic a standard outlet similar to plug receptacles 180 discussed above. Moreover, vapor-emitting device 400, in various embodiments, includes a power source 490 similar to power source 190 discussed above.

Various embodiments of vapor-emitting device 400 function such that as volatizable material 450 is evaporated, buoyant conductive material 454 is caused to move towards funnel 458. As volatizable material 450 is further evaporated, funnel 458 directs buoyant conductive material 454 towards electrodes 430b and 435b. When volatizable material 450 is sufficiently evaporated (or caused to be evaporated), buoyant conductive material 454 will connect electrodes 430b and 435b, thus completing the end of use indicator circuit. When the end of use indicator circuit is completed, the end of use indicator (e.g., light 460, audible device 470, and/or the like) is actuated (e.g., illuminated when the end of use indicator is light 460, and/or emits a continuous or intermittent sound when the end of use indicator is audible device 470 (i.e., a speaker)) to alert the user that refill portion 420 or vapor-emitting device 400 needs to be replaced.

Figure 5:
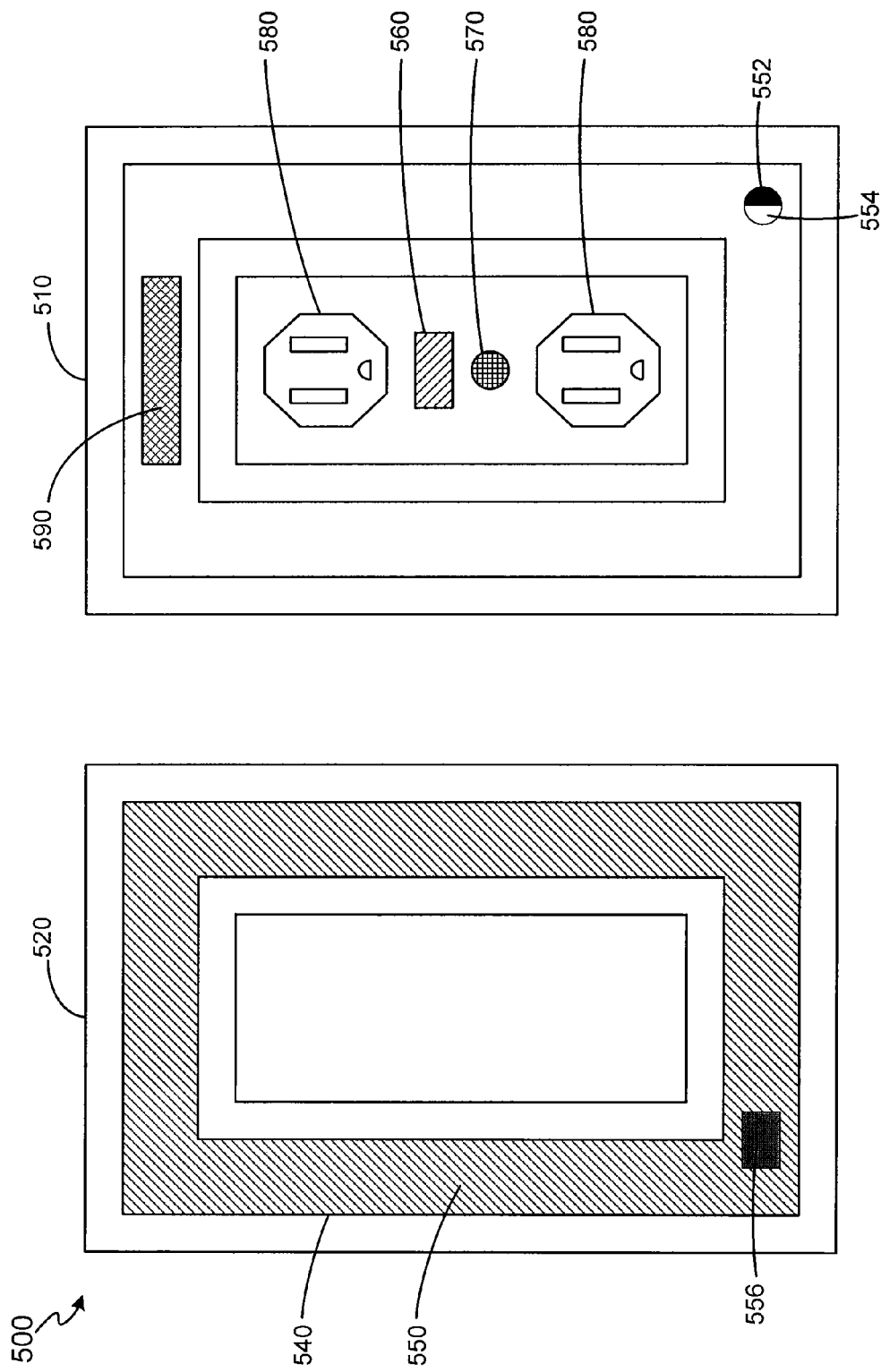
FIG. 5 is a diagram of an exemplary embodiment of a vapor-emitting device including a non-intrusive end of use indicator.

FIG. 5 is a diagram of one exemplary embodiment of a vapor-emitting device 500 including a non-intrusive end of use indicator. Vapor-emitting device 500 may be any device and/or components known in the art capable of evaporating a volatizable material or causing a volatizable material to be evaporated similar to vapor-emitting device 100 discussed above.

In one exemplary embodiment, vapor-emitting device 500 includes a non-refill portion 510 and a refill portion 520. Non-refill portion 510, in one embodiment, includes an infrared light source 552, wherein infrared light source 552 is any light, device, and/or components capable of emitting infrared light. In another exemplary embodiment, non-refill portion 510 includes an infrared light sensor 554, wherein infrared light sensor 554 is any device and/or components known in the art capable of detecting infrared light. In accordance with an aspect of one exemplary embodiment, infrared light sensor 554 is a photodiode.

Refill portion 520 includes a reservoir 540 to store a volatizable material 550 to be evaporated by or caused to be evaporated within vapor-emitting device 500, wherein volatizable material 550 may be any volatizable material known in the art capable of, for example, altering the scent in an environment (e.g., a fragrance) and/or discouraging insects and other creatures from being present in the environment (e.g., an insecticide, an insect repellant, and the like).

In accordance with another exemplary embodiment, volatizable material 550 includes an infrared light absorbing material. Examples of infrared light absorbing materials suitable for use in volatizable material 550 include, but are not limited to, dyes based on tetrakis amminium structures such as the Epolite series of infrared absorbent dyes. In addition, the invention contemplates that volatizable material 550 may include any material capable of preventing infrared light from passing through voltaizable material 550.

In still another exemplary embodiment, vapor-emitting device 500 includes a reflective material 556 oriented to reflect infrared light emitted from infrared light source 552 to infrared light sensor 554. Reflective material 556 may be oriented within reservoir 540 and/or on refill portion 520 so long as infrared light emitted from infrared light source 552 is capable of being reflected to infrared light sensor 554.

Vapor-emitting device 500 also includes an active end of use indicator to alert a user that reservoir 540 includes a low level of volatizable material 550 and/or reservoir 540 is empty similar to embodiments of the end of use indicator discussed above. In one exemplary embodiment, the end of use indicator is a light 560 similar to light 160 discussed above. In another exemplary embodiment, the end of use indicator is an audible device 570 similar to audible device 170 discussed above. Furthermore, vapor-emitting 500 may include both light 560 and audible device 570 similar to embodiments of vapor-emitting device 100 discussed above. In addition, vapor-emitting device 500 may include one or more plug receptacles 580, and/or may be configured to mimic a standard outlet similar to plug receptacles 180 discussed above. Moreover, vapor-emitting device 500, in various embodiments, includes a power source 590 similar to power source 190 discussed above.

Various embodiments of vapor-emitting device 500 function such that when sufficient volatizable material 550 is present within reservoir 540, infrared light emitted from infrared light source 552 is substantially prevented from being reflected by reflective material 556 to infrared light sensor 554. In other words, the infrared light is substantially absorbed by volatizable material 150 such that infrared light sensor 554 does not detect any infrared light. As volatizable material 550 is substantially or completely evaporated, infrared light is reflected by reflective material 556 to infrared light sensor 554. When infrared light sensor 554 detects infrared light, the end of use indicator (e.g., light 560, audible device 570, and/or the like) is actuated (e.g., illuminated when the end of use indicator is light 560, and/or emits a continuous or intermittent sound when the end of use indicator is audible device 570 (i.e., a speaker)) to alert the user that refill portion 520 or vapor-emitting device 500 needs to be replaced.

FIG. 6 is a diagram of another exemplary embodiment of a vapor-emitting device 600 including a non-intrusive end of use indicator. Vapor-emitting device 600 may be any device and/or components known in the art capable of evaporating a volatizable material or causing a volatizable material to be evaporated similar to vapor-emitting device 100 discussed above.

In one exemplary embodiment, vapor-emitting device 600 includes a non-refill portion 610 and a refill portion 620. Non-refill portion 610, in one embodiment, includes an infrared light source 652, wherein infrared light source 652 is any light, device, and/or components capable of emitting infrared light. Non-refill portion 610, in another embodiment, includes an infrared light sensor 654, which may be any device and/or components capable of detecting infrared light. In accordance with an aspect of one exemplary embodiment, infrared light sensor 654 is a photodiode. Furthermore, infrared light sensor 654 is suitably oriented on non-refill portion 610 such that infrared light emitted from infrared light source 652 is capable of being reflected to infrared light sensor 654.

In accordance with one exemplary embodiment, refill portion 620 includes a reservoir 640 to store a volatizable material 650 to be evaporated by or caused to be evaporated within vapor-emitting device 600. Volatizable material 650 may be any volatizable material known in the art capable of, for example, altering the scent in an environment (e.g., a fragrance) and/or discouraging insects and other creatures from being present in the environment (e.g., an insecticide, an insect repellant, and the like). In accordance with another exemplary embodiment, volatizable material 650 includes an infrared light reflecting material. Examples of infrared light reflecting materials suitable for use in volatizable material 650 include, but are not limited to, titanium dioxide, gold plating, and other reflective surface or blend materials that include infrared spectra that indicate reflection at a desired wavelength. In addition, the invention contemplates that volatizable material 650 may include any material capable of suitably reflecting infrared light.

Vapor-emitting device 600 also includes an active end of use indicator to alert a user that reservoir 640 includes a low level of volatizable material 650 and/or reservoir 640 is empty similar to embodiments of the end of use indicator discussed above. In one exemplary embodiment, the end of use indicator is a light 660 similar to light 160 discussed above. In another exemplary embodiment, the end of use indicator is an audible device 670 similar to audible device 170 discussed above. Furthermore, vapor-emitting 600 may include both light 660 and audible device 670 similar to embodiments of vapor-emitting device 100 discussed above. In addition, vapor-emitting device 600 may include one or more plug receptacles 680, and/or may be configured to mimic a standard outlet similar to plug receptacles 180 discussed above. Moreover, vapor-emitting device 600, in various embodiments, includes a power source 690 similar to power source 190 discussed above.

Various embodiments of vapor-emitting device 600 function such that when sufficient volatizable material 650 is present within reservoir 640, infrared light emitted from infrared light source 652 is substantially reflected by volatizable material 650 towards infrared light sensor 654. As volatizable material 650 is evaporated, infrared light is no longer reflected to infrared light sensor 654. When infrared light sensor 654 no longer detects infrared light, the end of use indicator (e.g., light 660, audible device 670, and/or the like) is actuated (e.g., illuminated when the end of use indicator is light 660, and/or emits a continuous or intermittent sound when the end of use indicator is audible device 670 (i.e., a speaker)) to alert the user that refill portion 620 or vapor-emitting device 600 needs to be replaced.

Figure 7:
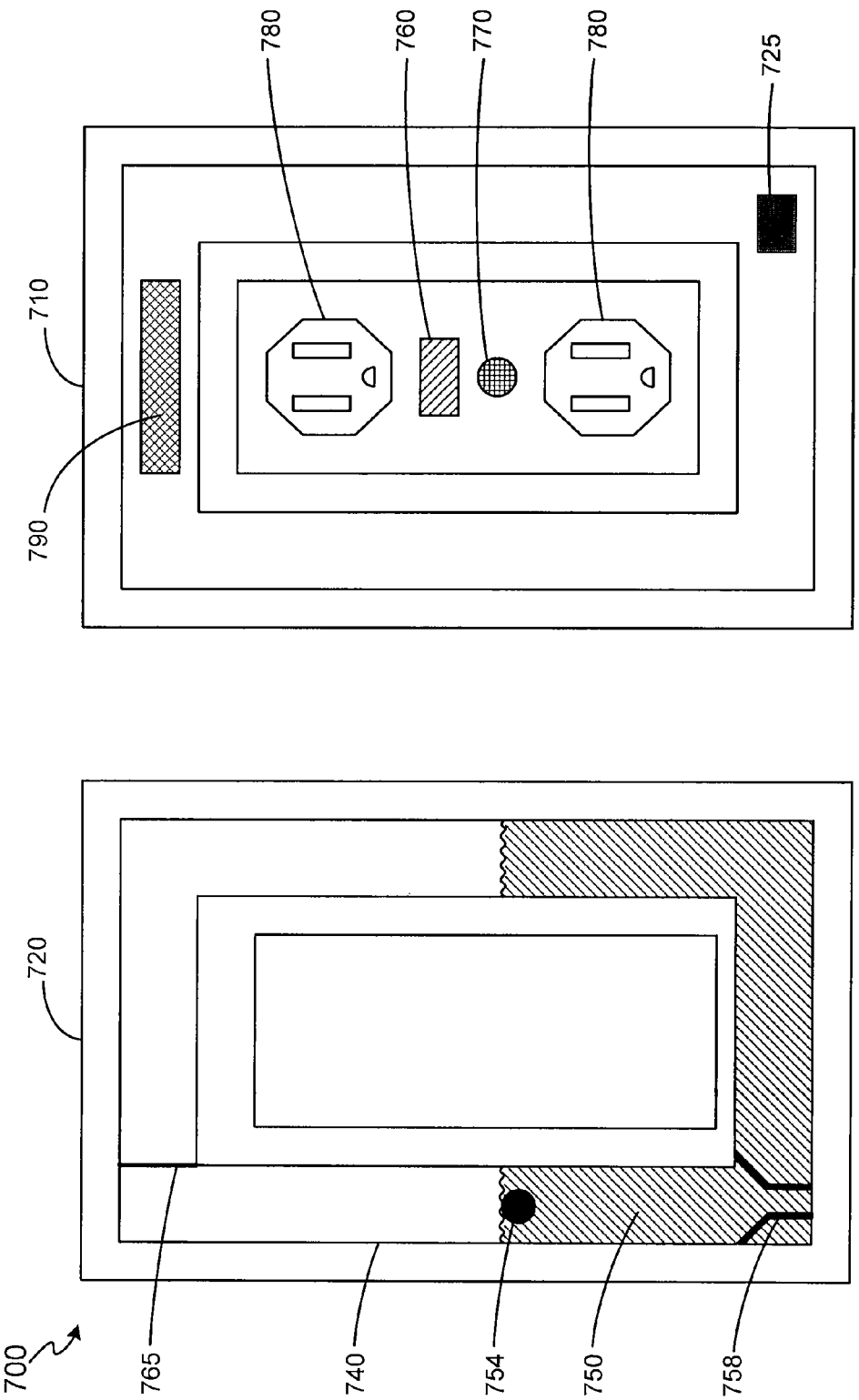
FIG. 7 is a diagram of yet another exemplary embodiment of a vapor-emitting device including a non-intrusive end of use indicator.

FIG. 7 is a diagram of yet another exemplary embodiment of a vapor-emitting device 700 including a non-intrusive end of use indicator. Vapor-emitting device 700 may be any device and/or components known in the art capable of evaporating a volatizable material or causing a volatizable material to be evaporated similar to vapor-emitting device 100 discussed above. Similar to FIG. 1, FIG. 7 illustrates an anterior view of one embodiment of a non-refill portion 710, and a posterior view of one embodiment of a refill portion 720.

Non-refill portion 710, in one exemplary embodiment, includes one or more magnetic sensors 725. Magnetic sensor 725 may be any sensor, device, and/or component(s) capable of detecting a magnetic device and actuating an end of user indicator when a magnetic substance is detected.

In one exemplary embodiment, a reservoir 740 is included as at least a portion of refill portion 720. In accordance with an exemplary embodiment, reservoir 740 stores a volatizable material 750 to be evaporated by or caused to be evaporated within vapor-emitting device 700. Volatizable material 750 may be any volatizable material known in the art capable of, for example, altering the scent in an environment (e.g., a fragrance) and/or discouraging insects and other creatures from being present in the environment (e.g., an insecticide, an insect repellant, and the like).

In another exemplary embodiment, reservoir 740 also includes a buoyant magnetic material 754. Buoyant magnetic material 754 may be any magnetic material capable of floating on/within volatizable material 750 and capable of being detected by magnetic sensor 725, and may include any suitable shape (e.g., a sphere). Examples of buoyant magnetic material 754 include, but are not limited to, the buoyant materials discussed above, wherein the material(s) include rare earth magnets and/or any other magnetic material such that the total density of the object is less than that of volatizable material 750. Reservoir 740, in yet another exemplary embodiment, includes a funnel 758 configured to direct buoyant magnetic material 754 towards magnetic sensor 725 as volatizable material 750 is evaporated or caused to be evaporated. Notably, magnetic sensor 725 may be oriented in any manner that allows buoyant magnetic material 754 to contact magnetic sensor 725 via funnel 758 as volatizable material 750 is vaporated or caused to be evaporated.

In yet another exemplary embodiment, reservoir 740 includes a barrier 765 to prevent buoyant magnetic material 754 from entering areas of reservoir 740 that will not direct buoyant magnetic material 754 towards funnel 758. In various exemplary embodiments, funnel 758 and/or barrier 765 include pours/apertures similar to embodiments of funnel 458 and/or barrier 465 discussed above.

Vapor-emitting device 700 also includes an active end of use indicator to alert a user that reservoir 740 includes a low level of volatizable material 750 and/or reservoir 740 is empty, similar to embodiments of the end of use indicator discussed above. In one exemplary embodiment, the end of use indicator is a light 760 similar to light 160 discussed above. In another exemplary embodiment, the end of use indicator is an audible device 770 similar to audible device 170 discussed above. Furthermore, vapor-emitting 700 may include both light 760 and audible device 770 similar to embodiments of vapor-emitting device 100 discussed above. In addition, vapor-emitting device 700 may include one or more plug receptacles 780, and/or may be configured to mimic a standard outlet similar to plug receptacles 180 discussed above. Moreover, vapor-emitting device 700, in various embodiments, includes a power source 790 similar to power source 190 discussed above.

Various embodiments of vapor-emitting device 700 function such that as volatizable material 750 is evaporated, buoyant magnetic material 754 is caused to move towards funnel 758. As volatizable material 750 is further evaporated, funnel 758 directs buoyant conductive material 754 towards magnetic sensor 725. When volatizable material 750 is sufficiently evaporated or caused to be evaporated, buoyant magnetic material 754 will be sensed by magnetic sensor 725, and the end of use indicator (e.g., light 760, audible device 770, and/or the like) is actuated (e.g., illuminated when the end of use indicator is light 760, and/or emits a continuous or intermittent sound when the end of use indicator is audible device 770 (i.e., a speaker)) to alert the user that refill portion 720 or vapor-emitting device 700 needs to be replaced.

Figure 8:
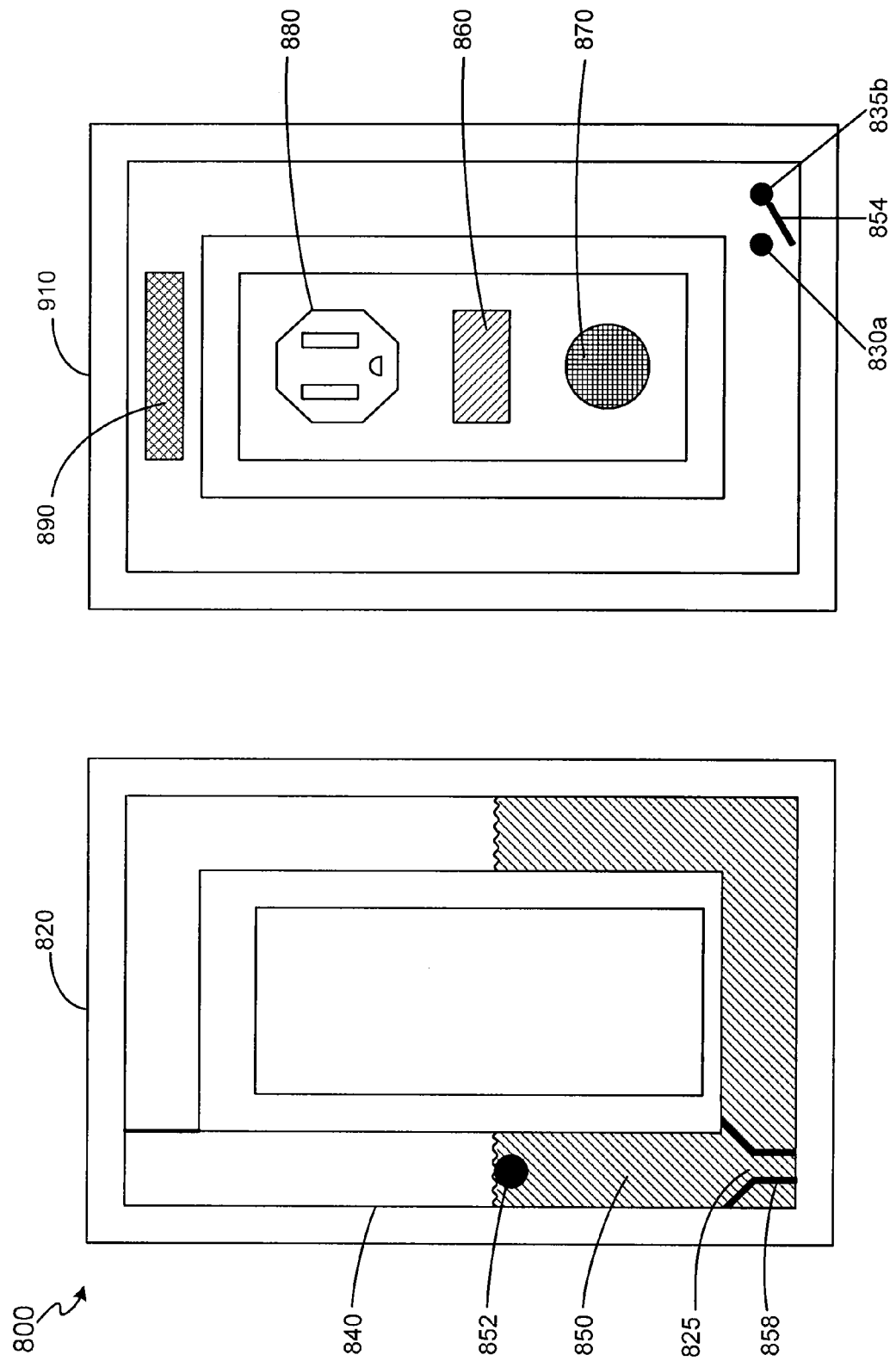
FIG. 8 is a diagram of still another exemplary embodiment of a vapor-emitting device including a non-intrusive end of use indicator.

FIG. 8 is a diagram of still another exemplary embodiment of a vapor-emitting device 800 including a non-intrusive end of use indicator. Vapor-emitting device 800 may be any device and/or components known in the art capable of evaporating a volatizable material or causing a volatizable material to be evaporated similar to vapor-emitting device 100 discussed above. Similar to FIG. 1, FIG. 8 illustrates an anterior view of one embodiment of a non refill portion 810, and a posterior view of one embodiment of a refill portion 820.

Non-refill portion 810, in one exemplary embodiment, includes an electrode 830a similar to electrode 130a discussed above, and a second electrode 835a similar to electrode 135a discussed above. Electrodes 830a and 835a, in one exemplary embodiment, are oriented adjacent to a reservoir 840 included within refill portion 820 when refill portion 810 is appropriately connected to non-refill portion 820. Furthermore, a conducting wire 854 is connected to one of electrode 830a or electrode 835a. Conducting wire 854 may be formed of any suitable material known in the art capable of conducting current. For example, conducting wire 854 may be copper, aluminum, and the like. Moreover, conducting wire 854 is oriented such that a magnetic field is capable of attracting in a manner which will connect electrode 830a to electrode 835a.

In accordance with one exemplary embodiment, reservoir 840 stores a volatizable material 850 to be evaporated by or caused to be evaporated within vapor-emitting device 800. Volatizable material 850 may be any volatizable material known in the art capable of, for example, altering the scent in an environment (e.g., a fragrance) and/or discouraging insects and other creatures from being present in the environment (e.g., an insecticide, an insect repellant, and the like).

In another exemplary embodiment, reservoir 840 also includes a buoyant magnetic material 852 in it. Buoyant magnetic material 852 may be any magnetic material capable of floating on/within volatizable material 850, and may include any suitable shape (e.g., a sphere) similar to buoyant magnetic material 754 discussed above.

Reservoir 840, in yet another exemplary embodiment, includes a funnel 858 configured to direct buoyant magnetic material 852 towards the focus 875 of funnel 858 as volatizable material 850 is evaporated or caused to be evaporated. In one exemplary embodiment, funnel 858 (and thus focus 875) is oriented such that when buoyant magnetic material 852 is located at focus 875 conductive wire 854 is attracted to buoyant magnetic material 852, and conductive wire 854 contacts both electrode 830a and electrode 835a.

In another embodiment, reservoir 840 includes a barrier 865 to prevent buoyant magnetic material 852 from entering areas of reservoir 840 that will not direct buoyant magnetic material 852 towards funnel 858. In various exemplary embodiments, funnel 858 and/or barrier 865 include pours/apertures similar to embodiments of funnel 458 and/or barrier 465 discussed above.

Vapor-emitting device 800 also includes an active end of use indicator to alert a user that reservoir 840 includes a low level of volatizable material 850 and/or reservoir 840 is empty, similar to embodiments of the end of use indicator discussed above. In one exemplary embodiment, the end of use indicator is a light 860 similar to light 160 discussed above. In another exemplary embodiment, the end of use indicator is an audible device 870 similar to audible device 170 discussed above. Furthermore, vapor-emitting 800 may include both light 860 and audible device 870 similar to embodiments of vapor-emitting device 100 discussed above. In addition, vapor-emitting device 800 may include one or more plug receptacles 880, and/or may be configured to mimic a standard outlet similar to plug receptacles 180 discussed above. Moreover, vapor-emitting device 800, in various embodiments, includes a power source 890 similar to power source 190 discussed above.

Various embodiments of vapor-emitting device 800 function such that as volatizable material 850 is evaporated, buoyant magnetic material 852 is caused to move towards funnel 858. As volatizable material 850 is further evaporated, funnel 858 directs buoyant conductive material 852 towards focus 875. When volatizable material 850 is sufficiently evaporated or caused to be evaporated, buoyant magnetic material 852 will eventually be located at focus 875 and cause conductive wire 854 to contact both electrode 830a and electrode 835a, thus completing the end of use indicator circuit. When the end of use indicator circuit is completed, the end of use indicator (e.g., light 860, audible device 870, and/or the like) is actuated (e.g., illuminated when the end of use indicator is light 860, and/or emits a continuous or intermittent sound when the end of use indicator is audible device 870 (i.e., a speaker)) to alert the user that refill portion 820 or vapor-emitting device 800 needs to be replaced.

Notably, various embodiments of vapor-emitting devices 100-800 have been described as mimicking a standard electrical outlet. However, the present invention is not limited to such descriptions. In other words, vapor-emitting devices 100-800 may include any shape and/or configuration. Furthermore, vapor-emitting devices 100-800 may not include a refill portion as discussed, but may include the reservoir and its associated components as part of the non-refill portion.

FIG. 9 is a diagram of one exemplary embodiment of a vapor-emitting device 900 including a solar-powered, active end of use indicator. Vapor-emitting device 900 may be any device and/or components known in the art capable of evaporating a volatizable material or causing a volatizable material to be evaporated.

In one exemplary embodiment, vapor-emitting device 900 includes a refill portion 920 and a non-refill portion 910. Refill portion 920, in an exemplary embodiment, includes a wick 925 connected to a reservoir 940, similar to reservoir 140, configured to store a volatizable material 950, wherein volatizable material 950 may be any volatizable material known in the art capable of, for example, altering the scent in an environment (e.g., a fragrance) and/or discouraging insects and other creatures from being present in the environment (e.g., an insecticide, an insect repellant, and the like). In accordance with one exemplary embodiment, reservoir 940 also includes a buoyant magnetic material 952, similar to buoyant magnetic material 852 discussed above.

Non-refill portion 910, in an exemplary embodiment, includes an emitter pad 915, wherein emitter pad 915 may be any emitter pad known in the art and/or any device suitably configured to emit a vapor. Furthermore, non-refill portion 910 includes a magnetic sensor 954 similar to magnetic sensor 725 discussed above.

Vapor-emitting device 900 also includes an active end of use indicator to alert a user that reservoir 940 includes a low level of volatizable material 950 and/or reservoir 940 is empty, similar to embodiments of the end of use indicator discussed above. In one exemplary embodiment, the end of use indicator is a light 960 similar to light 160 discussed above. In another exemplary embodiment, the end of use indicator is an audible device 970 similar to audible device 170 discussed above. Furthermore, vapor-emitting 900 may include both light 960 and audible device 970 similar to embodiments of vapor-emitting device 100 discussed above. Moreover, vapor-emitting device 900, in various embodiments, includes a power source 990 similar to power source 190 discussed above. In the embodiment illustrated in FIG. 9, power source 990 is a solar cell.

Various embodiments of vapor-emitting device 900 function such that as volatizable material 950 is evaporated, buoyant magnetic material 952 is caused to move towards magnetic sensor 954. When volatizable material 950 is sufficiently evaporated or caused to be evaporated, buoyant magnetic material 952 is sensed by magnetic sensor 954, and the end of use indicator (e.g., light 960, audible device 970, and/or the like) is actuated (e.g., illuminated when the end of use indicator is light 960, and/or emits a continuous or intermittent sound when the end of use indicator is audible device 970 (i.e., a speaker)) to alert the user that refill portion 920 or vapor-emitting device 900 needs to be replaced.

Benefits, other advantages, and solutions to problems have been described herein with regard to specific embodiments. However, the benefits, advantages, solutions to problems, and any element(s) that may cause any benefit, advantage, or solution to occur or become more pronounced are not to be construed as critical, required, or essential features or elements of any or all the claims or the invention. The scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described exemplary embodiments that are known to those of ordinary skill in the art are expressly incorporated herein by reference and are intended to be encompassed by the present claims.

The invention claimed is:

1. A vapor-emitting device comprising:
a reservoir comprising a volatizable material; and
an active end of use indicator in communication with the reservoir, wherein the active end of use indicator comprises:
a first electrode and a second electrode;
a buoyant conductive material located within the volatizable material and configured to form an electrical connection between the first electrode and the second electrode;
wherein the vapor emitting device comprises a non-refill portion and a refill portion; and
wherein the buoyant conductive material floats on the surface of the volatizable material and moves toward the first electrode and the second electrode as the volatizable material evaporates.

2. The vapor-emitting device according to claim 1, wherein the first electrode and the second electrode form a funnel configured to receive the buoyant conductive material.

3. The vapor-emitting device according to claim 1, wherein the buoyant conductive material is spherical.

4. The vapor-emitting device according to claim 1, wherein the buoyant conductive material is magnetized.

5. The vapor-emitting device according to claim 1, wherein the buoyant conductive material is solid.

6. The vapor-emitting device according to claim 1, wherein the buoyant conductive material is hollow.

7. The vapor-emitting device according to claim 1, wherein the buoyant conductive material is a blown structure.

8. The vapor-emitting device according to claim 1 wherein the non-refill portion contains the volatizable material.

9. The vapor-emitting device according to claim 1, wherein the reservoir comprises a refill for the vapor-emitting device.

10. The vapor-emitting device according to claim 1, wherein the reservoir and the active end of use indicator form a refill for the vapor-emitting device.

11. A vapor-emitting device comprising:
a reservoir comprising a volatizable material, wherein the volatizable material is an air freshener; and
an active end of use indicator in communication with the reservoir, wherein the active end of use indicator comprises:
a first electrode and a second electrode; and
a conductive material coupled to the first electrode and releasably attached to the second electrode wherein an electrical current is allowed to flow between the first electrode and the second electrode when the conductive material is attached to the second electrode; and
a buoyant material attached to the conductive material.

12. The vapor-emitting device according to claim 11, wherein the vapor-emitting device comprises a non-refill portion and a refill portion.

13. The vapor-emitting device according to claim 12, wherein the non-refill portion contains the volatizable material.

14. The vapor-emitting device according to claim 11, wherein the conductive material is a wire.

15. A vapor-emitting device comprising:
a reservoir comprising a volatizable material; and
an active end of use indicator in communication with the reservoir, wherein the active end of use indicator is configured to alert a user that the reservoir is at least one of substantially empty and includes an amount of volatizable material below a pre-determine level;
the active end of use indicator comprising:
a material coupled to a metal wire, wherein the material is buoyant in the volatizable material;
a first electrode coupled to the metal wire; and
a second electrode, wherein:
the metal wire is configured to contact the second electrode when the volatizable material is at least one of substantially evaporated and evaporated beyond a pre-determined level;
a completed circuit is formed when the metal wire contacts the second electrode, and
the active end of use indicator is configured to actuate when the completed circuit is formed.

16. The vapor-emitting device according to claim 15, wherein the buoyant material comprising a conductive material forms a substantially spherical shape.

* * * * *